United States Patent
Okada et al.

(10) Patent No.: US 6,897,037 B2
(45) Date of Patent: May 24, 2005

(54) PRE-TREATMENT KIT FOR SALIVA AND PRE-TREATMENT METHOD FOR SALIVA USING THE SAME

(75) Inventors: Junichi Okada, Tokyo (JP); Yumiko Kobayashi, Tokyo (JP)

(73) Assignee: GC Corporation, Tokyo (JP)

( * ) Notice: Subject to any disclaimer, the term of this patent is extended or adjusted under 35 U.S.C. 154(b) by 366 days.

(21) Appl. No.: 10/132,474

(22) Filed: Apr. 26, 2002

(65) Prior Publication Data

US 2003/0203423 A1 Oct. 30, 2003

(51) Int. Cl.$^7$ .......................... C12Q 1/04; G01N 33/53; C12N 1/00
(52) U.S. Cl. .......................... 435/34; 435/975; 435/885
(58) Field of Search .......................... 435/34, 975, 885

(56) References Cited

U.S. PATENT DOCUMENTS

2002/0197738 A1 * 12/2002 Matsumoto et al. ........ 436/518

OTHER PUBLICATIONS

Courtney et al, "Infection and immunity", V.59(5), p1661–1666, (May, 1991) (Abstract Only).*
Twetman et al, "Int. J Paediatric Denistry", V.9(2), p 93–98, (Jun. 1999) (Abstract Only).*

* cited by examiner

Primary Examiner—Louise N. Leary
(74) Attorney, Agent, or Firm—Oblon, Spivak, McClelland, Maier & Neustadt, P.C.

(57) ABSTRACT

To provide a pre-treatment kit for saliva and a pre-treatment method for saliva for identification and quantitation of mutans streptococci in human saliva by the immunochromatographic method, which can eliminate mucin in saliva and prevent mutans streptococci from chaining and aggregation in a simple method, the pre-treatment kit is constructed of (A) an aqueous solution containing sodium hydroxide, (B) a tris(hydroxymethyl)aminomethane buffer solution containing tartaric acid and/or citric acid, and (C) a nonionic surfactant and/or an amphoteric surfactant, wherein the component (C) is previously mixed with or prepared separately from the component (A) and/or the component (B), and further (D) a pH indicator having a color transition range of pH 5 to 9 is previously mixed with or prepared separately from the component (A) or the component (A) having the component (C) previously mixed therewith, and/or the component (B) or the component (B) having the component (C) previously mixed therewith. According the pre-treatment method, the respective components of the pre-treatment kit is added dropwise into and mixed with saliva in an arbitrary order.

12 Claims, No Drawings

PRE-TREATMENT KIT FOR SALIVA AND PRE-TREATMENT METHOD FOR SALIVA USING THE SAME

BACKGROUND OF THE INVENTION

1. Field of the Invention

The present invention relates to a pre-treatment kit for saliva and a pre-treatment method for saliva using the kit, which are used for identification and quantitation of a bacteria belongs to mutans streptococci that is one of cariogenic bacteria in human saliva, by the immunochromatographic method utilizing an antigen-antibody reaction.

2. Description of the Conventional Art

It is known that the presence of mutans streptococci in a human oral cavity is closely related to the generation of dental caries. If the presence or absence or the amount of mutans streptococci in the human oral cavity could be examined simply, it would become possible to grasp a disease risk or the current disease state. Thus, an extremely large number of people should possibly enjoy such benefits.

Hitherto, an examination utilizing an antigen-antibody reaction has been carried out for the examination of bacteria. For example, an enzymatic antibody method is a method for identification and quantitation by a color development density using an enzyme. However, this method requires not only a special washer and a complicated and precise operation for dealing with an antibody or a sample but also an incubator for achieving an enzymatic reaction. Further, a fluorescent antibody method is a method for labeling an antibody with a fluorescent dyestuff to dye specifically an antigen having reacted with the antibody. However, this method is not general because it requires a fluorescent microscope as an assay instrument.

For these reasons, a number of methods utilizing an antigen-antibody reaction simply have been proposed. For example, assay methods utilizing chromatography, as disclosed in U.S. Pat. Nos. 5,591,645, 4,855,240, 4,435,504 and 4,980,298, Japanese Patent Laid-Open Nos. 145459/1986 and 160388/1994, and so on, are a method that is superior in simplicity, upon which the presence or absence or the amount of an antigen can be known only by incorporating a collected body fluid into a test solution containing the antibody for the purpose of the identification and quantitation, and then infiltrating it into a test appliance. These methods are called generally an immunochromatographic method. In such methods, a specific antibody that attaches only to a target antigen (this antibody will be simply referred to "specific antibody", hereinafter) is infiltrated into one end of a porous membrane (a pore diameter: several tens $\mu$m) such as nitrocellulose, and another specific antibody similarly attaching only to a specific antigen is infiltrated in a stripe form into the middle of the porous membrane and fixed to the porous membrane. The specific antibody infiltrated into one end of the porous membrane is colored with particles of, e.g., colloidal gold in advance. When a sample solution is infiltrated into one end of the porous membrane where the specific antibody is present, so far as an antigen that is reactive with the specific antibody is present in the sample solution, the antigen is coupled with the specific antibody and moves in the state of attaching the coloring particles by the capillary action in the porous membrane toward the opposite end to the side into which the sample solution is infiltrated. During the movement, when the antigen passes through a portion where another specific antibody is fixed in a stripe form, the specific antibody on the porous membrane traps the antigen, whereby a stripe-like blot appears on the porous membrane. Thus, the presence of the target antigen in the sample and its amount can be known.

If such a technology were applied, it would appear possible to undergo the identification and quantitation of the above-described intraoral mutans streptococci. However, actually, such has not yet been put into practical use because of the presence of a problem as described below. That is, a sample that can be used in the immunochromatographic method should be able to pass in principle through the porous membrane by the capillary action. However, since a major sample that is used for the examination of intraoral bacteria such as mutans streptococci is saliva, a highly viscous substance that is called mucin present in the saliva clogs pores of the porous membrane. Also, the mucin acts to aggregate epithelium-attaching cells present in the saliva, which have come off and dropped from an oral mucosa surface. Accordingly, such a substance clogs the pores of the porous membrane so that the mutans streptococci cannot pass through the porous membrane.

Also, in addition to the matter of mucin, there is a problem to make the assay of mutans streptococci becomes difficult. That is, the objective mutans streptococci are bacteria having a diameter of about 1 $\mu$m in terms of a single body. However, since the mutans streptococci are streptococci, from ten to twenty or more of them are often chained with each other, which causes to hinder the movement within the porous membrane. Moreover, the mutans streptococci generate viscous glucan from sucrose in foods, whereby they are often aggregated vigorously to each other. Still further, the chaining and aggregation of the mutans streptococci not only cause clogging of the porous membrane but also reduce the surface areas of the streptococci and influence the number of antigens present on the surfaces of the mutans streptococci, resulting in lowering in the assay precision.

SUMMARY OF THE INVENTION

The invention is aimed to provide a pre-treatment kit for saliva and a pre-treatment method for saliva using the kit for identification and quantitation of a mutans streptococcus that is one of extra cariogenic bacteria in human saliva, by the immunochromatographic method, which can eliminate mucin present in saliva and prevent mutans streptococci from chaining and aggregation in a simple method.

In order to achieve the foregoing aim, we, the present inventors made extensive and intensive investigations. As a result, it has been found that when the treatment is carried out using a specific acid and alkaline solution, they dissolve mucin and glucan present in saliva and act outer membranes of mutans streptococci, thereby suppressing the aggregation of mutans streptococci; that when a specific surfactant is further used, it makes proteins present in the mutans streptococci soluble, thereby enabling the mutans streptococci to pass smoothly through a porous membrane; and that when a pH indicator having a color transition range within a specific pH range is used, it is possible to confirm with ease whether or not the system is in a state that an antigen-antibody reaction is carried out, leading to accomplishment of the present invention.

Specifically, the pre-treatment kit for saliva according to the present invention is characterized by comprising an aqueous solution containing sodium hydroxide; a tris (hydroxymethyl)aminomethane buffer solution containing tartaric acid and/or citric acid; and a nonionic surfactant and/or an amphoteric surfactant, wherein the surfactant is previously mixed with the aqueous solution and/or the buffer solution, or is prepared separately from the aqueous solution and the buffer solution.

Preferably, a pH indicator having a color transition range of pH 5 to 9 is mixed with the aqueous solution or the aqueous solution having the surfactant previously mixed therewith, and/or the buffer solution or the buffer solution having the surfactant previously mixed therewith, or is separated from the aqueous solution or the aqueous solution having the surfactant previously mixed therewith, and the buffer solution or the buffer solution having the surfactant previously mixed therewith.

Preferably, the nonionic surfactant as the surfactant is one member or a mixture of two or more members selected from the group consisting of polyethylene glycol monooctylphenyl ether, n-octyl-β-D-glucoside, n-heptyl-β-D-thioglucoside, n-octyl-β-D-thioglucoside, nonylphenoxypolyethoxy ethanol, octylphenoxypolyethoxy ethanol, and polyoxyethylene sorbitan monooleate; the amphoteric surfactant as the surfactant is one member or a mixture of two members selected from the group consisting of 3-[(3-cholamidopropyl)-dimethylammonio]-1-propanesulfonate and 3-[(3-cholamidopropyl)-dimethylammonio]-1-hydroxypropanesulfonate; and the pH indicator having a color transition range of pH 5 to 9 is one member selected from the group consisting of Methyl Red, azolitmin, p-nitrophenol, m-nitrophenol, Bromocresol Purple, Bromophenol Red, Chlorophenol Red, Phenol Red, Neutral Red, Bromothymol Blue, phenolphthalein, and Thymolphthalein.

Also, the pre-treatment method for saliva according to the present invention is a pre-treatment method for identification and quantitation of mutans streptococci by the immunochromatographic method, which comprises adding dropwise and mixing an aqueous solution containing sodium hydroxide, a tris(hydroxymethyl)aminomethane buffer solution containing tartaric acid and/or citric acid, and a nonionic surfactant and/or an amphoteric surfactant into and with saliva in an arbitrary order, or adding dropwise and mixing the aqueous solution and the buffer solution, with at least one of which the surfactant is mixed, into and with saliva in an arbitrary order, to adjust the pH into 5 to 9. It is preferred to use a mixture of the aqueous solution and/or the buffer solution to be added dropwise and mixed, or the aqueous solution and/or the buffer solution, with at least one of which the surfactant is previously mixed, and a pH indicator having a color transition range of pH 5 to 9. Also, it is preferred that, during the dropwise addition of the aqueous solution and the buffer solution in dropwise addition and mixing of the aqueous solution, the buffer solution and the surfactant, or during the dropwise addition of the aqueous solution and the buffer solution in dropwise addition and mixing of the aqueous solution and the buffer solution, with at least one of which the surfactant is previously mixed, a pH indicator having a color transition range of pH 5 to 9 is previously added dropwise prior to the dropwise addition of the aqueous solution or the buffer solution to be added dropwise later.

DESCRIPTION OF THE PREFERRED EMBODIMENTS

The aqueous solution (A) containing sodium hydroxide, which is used for the pre-treatment kit for saliva and the pre-treatment method for saliva according to the present invention, acts on mucin and glucan present in outer membranes of mutans streptococci in saliva, thereby suppressing the aggregation of the mutans streptococci and making the mutans streptococci as antigens easy to move within a porous membrane. It is important to use sodium hydroxide as an alkaline solution. Sodium carbonate, disodium hydrogenphosphate, and the like are not suitable. In other words, it is impossible to examine the mutans streptococci by using aqueous alkaline solutions other than sodium hydroxide. This is because it is estimated that aqueous alkaline solutions other than sodium hydroxide possibly give an impediment to the structure of the antigens of the mutans streptococci.

The tris(hydroxymethyl)aminomethane buffer solution (B) containing tartaric acid and/or citric acid, which is used for the pre-treatment kit for saliva and the pre-treatment method for saliva according to the present invention, suppresses the chaining of the mutans streptococcus and acts to make the mutans streptococci as antigens easy to move within the porous membrane. It is important to use tartaric acid and/or citric acid as an acid. Other acids such as hydrochloric acid, sulfuric acid, nitric acid, acetic acid, lactic acid, and maleic acid are not suitable. Even when such acids other than tartaric acid and citric acid are used in combination with sodium hydroxide, a desired sensitivity to the examination cannot be attained. This is because it is estimated that acids other than tartaric acid and citric acid possibly give an impediment to the structure of the antigens of the mutans streptococci. In the pre-treatment kit for saliva and the pre-treatment method for saliva according to the present invention, it is necessary to use a buffer because a neutralization reaction occurs between the sodium hydroxide and the tartaric acid and/or citric acid. It is important that the aqueous solution containing tartaric acid and/or citric acid contains tris(hydroxymethyl)aminomethane as the buffer. In order to attain effectively the buffer action, it is necessary to use tris(hydroxymethyl)aminomethane in the side of the solution containing tartaric acid and/or citric acid. As a matter of course, tris(hydroxymethyl)aminomethane may be used simultaneously in the side of the aqueous sodium hydroxide solution. However, at this time, it is already confirmed that the buffer action is not attained by other buffers such as a combination of sodium bicarbonate and sodium carbonate, or a combination of citric acid and sodium citrate.

It is preferred that the concentrations of sodium hydroxide and of tartaric acid and/or citric acid are 0.01 N or more, respectively. When each of the concentrations of sodium hydroxide and of tartaric acid and/or citric acid is less than 0.01 N, not only the effect that will be brought by each of the components tends to be hardly attained, but also clogging of the porous membrane is liable to occur. Actually, the higher the concentrations of sodium hydroxide and of tartaric acid and/or citric acid, the more advantageous it is from the standpoint of the detection sensitivity. Also, in the pre-treatment kit for saliva according to the present invention, it is necessary that the aqueous solution (A) containing sodium hydroxide and the tris(hydroxymethyl)aminomethane buffer solution (B) containing tartaric acid and/or citric acid are separated from each other because a neutralization action is present between them.

The nonionic surfactant and/or the amphoteric surfactant (C), which is used for the pre-treatment kit for saliva and the pre-treatment method for saliva according to the present invention, acts to make proteins present on the surfaces of the mutans streptococci soluble and enable the mutans streptococci to pass smoothly through the porous membrane. Hitherto, according to the immunochromatographic method, an ionic surfactant is often used such that the sample solution or antigen solution can smoothly move within a test appliance. However, the surfactant (C) that is used in the pre-treatment kit for saliva and the pre-treatment method for saliva for undergoing the identification and quantitation of the mutans streptococcus antigen according to the present invention is required to be a nonionic surfactant and/or an amphoteric surfactant from the experimental results. When an anionic surfactant such as sodium lauryl sulfate and sodium dodecylbenzenesulfonate, or a cationic surfactant, is used, the specific antibody cannot detect the antigen.

The surfactant (C) that is used in the present invention is not particularly limited so far as it is a nonionic surfactant and/or an amphoteric surfactant, and any of those that are generally used as a solubilizing agent of membrane proteins can be used. However, there is a difference in the detection sensitivity of the mutans streptococci antigen depending on the kind of the nonionic surfactant and/or the amphoteric surfactant used. Especially, it is preferred from the viewpoint of the detection sensitivity that the nonionic surfactant is one member or a mixture of two or more members selected from the group consisting of polyethylene glycol monooctylphenyl ether, n-octyl-$\beta$-D-glucoside, n-heptyl-$\beta$-D-thioglucoside, and n-octyl-$\beta$-D-thioglucoside; and that the amphoteric surfactant is any one member or a mixture of two members selected from the group consisting of CHAPS (3-[(3-cholamidopropyl)-dimethylammonio]-1-propanesulfonate) and CHAPSO (3-[(3-cholamidopropyl)-dimethylammonio]-1-hydroxypropanesulfonate).

It is preferred to use the nonionic surfactant and/or the amphoteric surfactant (C) such that the concentration of the nonionic surfactant and/or the amphoteric surfactant (C) in the saliva sample after the treatment of saliva is 0.05 to 90% by weight. When the concentration of the nonionic surfactant and/or the amphoteric surfactant (C) in the saliva sample after the treatment of saliva is less than 0.05% by weight, the detection sensitivity by the antigen-antibody reaction disappears, whereas when it exceeds 90% by weight, the detection sensitivity by the antigen-antibody reaction is lowered, and hence, the both are not suitable.

In the pre-treatment kit for saliva according to the present invention, the nonionic surfactant and/or the amphoteric surfactant (C) may be provided separately from the aqueous solution (A) containing sodium hydroxide and the tris(hydroxymethyl)aminomethane buffer solution (B) containing tartaric acid and/or citric acid. In this case, the nonionic surfactant and/or the amphoteric surfactant (C) maybe in a form of an aqueous solution. Further, the nonionic surfactant and/or the amphoteric surfactant (C) may be provided in a state of a mixture with either one or both of the aqueous solution (A) containing sodium hydroxide and the tris(hydroxymethyl)aminomethane buffer solution (B) containing tartaric acid and/or citric acid. In this case, attention must be paid to the decomposition properties by an acid or an alkali.

As the pH indicator (D) having a color transition range of pH 5 to 9, which is used for the pre-treatment kit for saliva and the pre-treatment method for saliva according to the present invention, preferably used is one member selected from the group consisting of Methyl Red (transition range: 4.4 to 6.2), azolitmin (transition range: 5.0 to 8.0), p-nitrophenol (transition range: 5.0 to 7.0), m-nitrophenol (transition range: 6.4 to 8.8), Bromocresol Purple (transition range: 5.2 to 6.8), Bromophenol Red (transition range: 5.2 to 6.8), Chlorophenol Red (transition range: 5.2 to 6.8), Phenol Red (transition range: 6.4 to 8.0), Neutral Red (transition range: 6.8 to 8.0), Bromothymol Blue (transition range: 6.0 to 7.6), phenolphthalein (transition range: 8.0 to 10.0), and Thymolphthalein (transition range: 8.3 to 10.6). The pH indicator (D) may be used in an embodiment where it is mixed with the aqueous solution (A) or the aqueous solution (A) having the surfactant (C) previously mixed therewith, and/or the buffer solution (B) or the buffer solution (B) having the surfactant (C) previously mixed therewith. Alternatively, the pH indicator (D) may be used in an embodiment where it is separated from the aqueous solution (A) or the aqueous solution (A) having the surfactant (C) previously mixed therewith, and the buffer solution (B) or the buffer solution (B) having the surfactant (C) previously mixed therewith. Incidentally, since the amount of the pH indicator (D) to be used may be very small, it is not necessary to take into consideration any influence of the pH indicator (D) to the concentrations of the sodium hydroxide in the aqueous solution (A), the tartaric acid and/or citric acid in the buffer solution (B), and the surfactant (C).

The pre-treatment method for saliva according to the present invention is a method, which comprises adding dropwise and mixing the aqueous solution (A) containing sodium hydroxide, the tris(hydroxymethyl)aminomethane buffer solution (B) containing tartaric acid and/or citric acid, and the nonionic surfactant and/or the amphoteric surfactant (C) into and with saliva in an arbitrary order. For the purpose of simplifying this pre-treatment method, the nonionic surfactant and/or the amphoteric surfactant (C) may be added in advance to at least one of the aqueous solution (A) containing sodium hydroxide and the tris(hydroxymethyl) aminomethane buffer solution (B) containing tartaric acid and/or citric acid. Even in this case, as a matter of course, the nonionic surfactant and/or the amphoteric surfactant (C) may be added to the aqueous solution (A) containing sodium hydroxide and the tris(hydroxymethyl)aminomethane buffer solution (B) containing tartaric acid and/or citric acid in an arbitrary order.

Since the respective components, the aqueous solution (A) containing sodium hydroxide, the tris(hydroxymethyl) aminomethane buffer solution (B) containing tartaric acid and/or citric acid, and the nonionic surfactant and/or the amphoteric surfactant (C), that are used in the present invention, have a function independent on each other, they can be treated in an arbitrary order. However, the treatments are carried out such that the saliva after the treatments has a pH within a range from 5 to 9. This is because the antigen-antibody reaction is carried out within this pH range, and therefore, while varying depending upon the kind of the specific antibody, when the pH is outside the above-specified range, the specific antibody is separated from the antigen, or the specific antibody has a non-specific affinity, resulting in lowering the reliability of the measurement results.

The saliva sample treated by the pre-treatment kit for saliva and the pre-treatment method for saliva according to the present invention can be subjected to identification and quantitation of mutans streptococci by the antigen-antibody reaction using the immunochromatographic method as conventionally employed in the art. The specific antibody can be obtained by the usually employed methods. For example, one obtained according to a hybridoma-establishment method by cell fusion as proposed by Kohler and Milstein (G. Kohler and C. Milstein, "Continuous cultures of fused cells secreting antibody of predefined specificity", *Nature*, 256: 495–497, 1975) may be employed. Further, one obtained by merely immunizing an antigen to an animal and purifying the resulting serum may be employed.

The pre-treatment kit for saliva and the pre-treatment method for saliva according to the present invention will be described with reference to the following Examples, but it should not be construed that the present invention is limited thereto.

(1) Preparation of Reagents and Test Appliances:

1. Preparation of Specific Antibodies:

*Streptococcus mutans* (ATCC25175 strain) and *Streptococcus sobrinus* (ATCC33478 strain) as mutans streptococci were each cultivated, and their growth was stopped in an aqueous formaldehyde solution. These bacterial dispersions were each immunized as they were to a mouse, and two kinds of purified antibodies for each bacterium as described below were obtained according to a hybridoma-establishment method by cell fusion as proposed by Kohler and Milstein.

| | |
|---|---|
| SM1 antibody: | Specific antibody against *Streptococcus mutans* |
| SM2 antibody: | Specific antibody against *Streptococcus mutans* |
| SS1 antibody: | Specific antibody against *Streptococcus sobrinus* |
| SS2 antibody: | Specific antibody against *Streptococcus sobrinus* |

2. Labeling on Specific Antibodies:

A colloidal gold having a particle size of 40 nm was labeled on each of the SM2 and SS2 antibodies. As the colloidal gold, a commercially available one (made by British Biocell International) was used and diluted with a phosphate buffer solution having 1% of bovine serum albumin (a trade name: BSA, made by Sigma Chemical Company) and 1% of a nonionic surfactant (a trade name: Tween 20, made by Sigma Chemical Company) added thereto such that an antibody concentration was 0.1 µg/mL. The antibody solutions each labeled with a colloidal gold are called a colloidal gold-labeled SM2 antibody solution and a colloidal gold-labeled SS2 antibody solution, respectively.

3. Preparation of Porous Membrane for Immunochromatography:

As a porous membrane, used was a nitrocellulose membrane (a trade name: SXHF, made by Nihon Millipore Ltd.). This membrane was cut into a rectangle of 5 mm×40 mm. The SM1 antibody or the SS1 antibody was diluted in a 50 mM phosphate buffer solution containing 1% of bovine serum albumin into a concentration of 1 mg/mL. The antibody diluted solution was applied in a central portion of the nitrocellulose membrane perpendicular to the longitudinal direction using a micropipette, such that the application amount was about 1 mg/cm. On one end of this membrane, fixed was a 15 mm-square filter paper with a clip, to prepare an absorber. The thus prepared appliance was dried at 37° C. for 2 hours and kept in a desiccator until just before the use.

(2) Test Method by Immunochromatography:

1. Saliva is collected from a subject and treated by the pre-treatment kit for saliva.
2. 100 µL of the treated saliva is added to 25 µL of the colloidal gold-labeled SM2 antibody solution or the colloidal gold-labeled SS2 antibody solution.
3. One end of the porous membrane for chromatography having the antibody corresponding to the colloidal gold-labeled antibody applied thereonto, in this test solution to have the test solution infiltrated into the porous membrane and the presence or absence of occurrence of an antibody reaction is observed.

EXAMPLE 1

Saliva (100 µL) was treated in the following manner, to observe the presence or absence of occurrence of an antibody reaction. In this case, as the saliva, used was one having $2 \times 10^6$ (CFU/mL) of bacteria of Streptococcus mutans, as measured by a fluorometer, in the saliva. Further, as the porous membrane, used was one having the SM1 antibody applied thereto.

A 1.0 M tris(hydroxymethyl)aminomethane buffer solution containing 1.0 N sodium hydroxide was designated as a sodium hydroxide-containing aqueous solution (A solution), and a 1.0 M tris(hydroxymethyl)aminomethane buffer solution containing 1.0 N citric acid and having 5% by weight of polyethylene glycol monooctylphenyl ether (made by Wako Pure Chemical Industries, Ltd.) as a nonionic surfactant added thereto was designated as a citric acid-containing tris(hydroxymethyl)aminomethane buffer solution containing a nonionic surfactant (BC solution).

To 100 µL of the saliva, successively added were 20 µL of the A solution and 25 µL of the BC solution, to form a mixture. Also, to 100 µL of the saliva, successively added were 25 µL of the BC solution and about 20 µL of the A solution, to form a mixture. Each of the mixtures was tested by the immunochromatographic method. In any of the saliva samples after mixing, clogging of the porous membrane was not observed, and occurrence of the antibody reaction was confirmed.

EXAMPLE 2

Saliva (100 µL) was treated in the following manner, to observe the presence or absence of occurrence of an antibody reaction. In this case, as the saliva, used was one having $2 \times 10^6$ (CFU/mL) of bacteria of *Streptococcus sobrinus*, as measured by a fluorometer, in the saliva. Further, as the porous membrane, used was one having the SS1 antibody applied thereto.

A 1.0 M tris(hydroxymethyl)aminomethane buffer solution containing 1.0 N sodium hydroxide was designated as a sodium hydroxide-containing aqueous solution (A solution), and a 1.0 M tris(hydroxymethyl)aminomethane buffer solution containing 1.0 N citric acid and having 1% by weight of polyethylene glycol monooctylphenyl ether (made by Wako Pure Chemical Industries, Ltd.) as a nonionic surfactant added thereto was designated as a citric acid-containing tris(hydroxymethyl)aminomethane buffer solution containing a nonionic surfactant (BC solution).

To 100 µL of the saliva, successively added were 20 µL of the A solution and 15 µL of the BC solution, to form a mixture. Also, to 100 µL of the saliva, successively added were 15 µL of the BC solution and 20 µL of the A solution, to form a mixture. Each of the mixtures was tested by the immunochromatographic method. In any of the saliva samples after mixing, clogging of the porous membrane was not observed, and occurrence of the antibody reaction was confirmed.

EXAMPLE 3

Saliva (100 µL) was treated in the following manner, to observe the presence or absence of occurrence of an antibody reaction. In this case, as the saliva, used was one having $2 \times 10^6$ (CFU/mL) of bacteria of *Streptococcus mutans*, as measured by a fluorometer, in the saliva. Further, as the porous membrane, used was one having the SM1 antibody applied thereonto.

A 1.0 M tris(hydroxymethyl)aminomethane buffer solution containing 1.0 N sodium hydroxide and having 5% by weight of polyethylene glycol monooctylphenyl ether (made by Wako Pure Chemical Industries, Ltd.) as a nonionic surfactant added thereto was designated as a sodium hydroxide-containing aqueous solution containing a nonionic surfactant (AC solution), and a 1.5 M tris (hydroxymethyl) aminomethane buffer solution containing 1.0 N citric acid and having 5% by weight of polyethylene glycol monooctylphenyl ether (made by Wako Pure Chemical Industries, Ltd.) as a nonionic surfactant added thereto was designated as a citric acid-containing tris (hydroxymethyl)aminomethane buffer solution containing a nonionic surfactant (BC solution).

To 100 μL of the saliva, successively added were 15 μL of the BC solution and 20 μL of the AC solution, to form a mixture. The mixture was tested by the immunochromatographic method. In the saliva sample after mixing, clogging of the porous membrane was not observed, and occurrence of the antibody reaction was confirmed.

EXAMPLE 4

Saliva (100 μL) was treated in the following manner, to observe the presence or absence of occurrence of an antibody reaction. In this case, as the saliva, used was one having $2 \times 10^6$ (CFU/mL) of bacteria of *Streptococcus sobrinus*, as measured by a fluorometer, in the saliva. Further, as the porous membrane, used was one having the SS1 antibody applied thereonto.

A 1.0 M tris(hydroxymethyl)aminomethane buffer solution containing 1.0 N sodium hydroxide and having 1% by weight of polyethylene glycol monooctylphenyl ether (made by Wako Pure Chemical Industries, Ltd.) as a nonionic surfactant added thereto was designated as a sodium hydroxide-containing aqueous solution containing a nonionic surfactant (AC solution), and a 0.75 M tris (hydroxymethyl) aminomethane buffer solution containing 1.0 N citric acid was designated as a citric acid-containing tris(hydroxymethyl)aminomethane buffer solution (B solution).

To 100 μL of the saliva, successively added were 20 μL of the AC solution and 15 μL of the B solution, to form a mixture. The mixture was tested by the immunochromatographic method. In the saliva sample after mixing, clogging of the porous membrane was not observed, and occurrence of the antibody reaction was confirmed.

EXAMPLE 5

Saliva (100 μL) was treated in the following manner, to observe the presence or absence of occurrence of an antibody reaction. In this case, as the saliva, used was one having $2 \times 10^6$ (CFU/mL) of bacteria of *Streptococcus mutans*, as measured by a fluorometer, in the saliva. Further, as the porous membrane, used was one having the SM1 antibody applied thereonto.

A 1.0 M tris(hydroxymethyl)aminomethane buffer solution containing 1.0 N sodium hydroxide and having 1% by weight of n-octyl-β-D-glucoside (made by Wako Pure Chemical Industries, Ltd.) as a nonionic surfactant added thereto was designated as a sodium hydroxide-containing aqueous solution containing a nonionic surfactant (AC solution), and a 1.0 M tris(hydroxymethyl)aminomethane buffer solution containing 2.0 N citric acid was designated as a citric acid-containing tris (hydroxymethyl) aminomethane buffer solution (B solution).

To 100 μL of the saliva, successively added were 20 μL of the B solution and 6 μL of the AC solution, to form a mixture. The mixture was tested by the immunochromatographic method. In the saliva sample after mixing, clogging of the porous membrane was not observed, and occurrence of the antibody reaction was confirmed.

EXAMPLE 6

Saliva (100 μL) was treated in the following manner, to observe the presence or absence of occurrence of an antibody reaction. In this case, as the saliva, used was one having $2 \times 10^6$ (CFU/mL) of bacteria of *Streptococcus sobrinus*, as measured by a fluorometer, in the saliva. Further, as the porous membrane, used was one having the SS1 antibody applied thereonto.

A 0.75 M tris(hydroxymethyl)aminomethane buffer solution containing 1.0 N sodium hydroxide and having 1% by weight of polyethylene glycol monooctylphenyl ether (made by Wako Pure Chemical Industries, Ltd.) as a nonionic surfactant added thereto was designated as a sodium hydroxide-containing aqueous solution containing a nonionic surfactant (AC solution), and a 0.15 M tris (hydroxymethyl)aminomethane buffer solution containing 1.05 N citric acid was designated as a citric acid-containing tris(hydroxymethyl)aminomethane buffer solution (B solution).

To 100 μL of the saliva, successively added were 25 μL of the B solution and 20 μL of the AC solution, to form a mixture. The mixture was tested by the immunochromatographic method. In the saliva sample after mixing, clogging of the porous membrane was not observed, and occurrence of the antibody reaction was confirmed.

EXAMPLE 7

Saliva (100 μL) was treated in the following manner, to observe the presence or absence of occurrence of an antibody reaction. In this case, as the saliva, used was one having $2 \times 10^6$ (CFU/mL) of bacteria of *Streptococcus sobrinus*, as measured by a fluorometer, in the saliva. Further, as the porous membrane, used was one having the SS1 antibody applied thereonto.

A 1.0 M tris(hydroxymethyl)aminomethane buffer solution containing 1.0 N sodium hydroxide was designated as a sodium hydroxide-containing aqueous solution (A solution); a 1.0 M tris(hydroxymethyl)aminomethane buffer solution containing 1.05 N citric acid was designated as a citric acid-containing tris (hydroxymethyl) aminomethane buffer solution (B solution); and a sodium phosphate buffer solution containing 10% by weight of 3-[(3-cholamidopropyl)-dimethylammonio]-1-propanesulfonate (made by Sigma Chemical Company) as an amphoteric surfactant was designated as an amphoteric surfactant (C solution), respectively.

To 100 μL of the saliva, successively added were 20 μL of the A solution, 15 μL of the B solution, and 10 μL of the C solution, to form a mixture. The mixture was tested by the immunochromatographic method. In the saliva sample after mixing, clogging of the porous membrane was not observed, and occurrence of the antibody reaction was confirmed.

EXAMPLE 8

Using the saliva sample and the treatment kit for saliva as used in Example 7, to 100 μL of the saliva, successively added were 10 μL of the C solution, 15 μL of the B solution, and 20 μL of the A solution, to form a mixture. The mixture was tested by the immunochromatographic method. In the saliva sample after mixing, clogging of the porous membrane was not observed, and occurrence of the antibody reaction was confirmed.

EXAMPLE 9

Saliva (100 μL) was treated in the following manner, to observe the presence or absence of occurrence of an antibody reaction. In this case, as the saliva, used was one having $2 \times 10^6$ (CFU/mL) of bacteria of *Streptococcus sobrinus*, as measured by a fluorometer, in the saliva. Further, as the porous membrane, used was one having the SS1 antibody applied thereonto.

A 1.0 M tris(hydroxymethyl)aminomethane buffer solution containing 1.0 N sodium hydroxide was designated as a sodium hydroxide-containing aqueous solution (A solution); a 1.0 M tris(hydroxymethyl)aminomethane buffer solution containing 1.0 N tartaric acid was designated as a tartaric acid-containing tris(hydroxymethyl)aminomethane buffer solution (B solution); and a sodium phosphate buffer solution containing 10% by weight of polyethylene glycol monooctylphenyl ether (made by Wako Pure Chemical Industries, Ltd.) as a nonionic surfactant was designated as a nonionic surfactant (C solution), respectively.

To 100 μL of the saliva, successively added were 20 μL of the B solution, 10 μL of the C solution, and 20 μL of the A solution, to form a mixture. The mixture was tested by the immunochromatographic method. In the saliva sample after mixing, clogging of the porous membrane was not observed, and occurrence of the antibody reaction was confirmed.

EXAMPLE 10

Saliva (100 μL) was treated in the following manner, to observe the presence or absence of occurrence of an antibody reaction. In this case, as the saliva, used was one having $2 \times 10^6$ (CFU/mL) of bacteria of *Streptococcus sobrinus*, as measured by a fluorometer, in the saliva. Further, as the porous membrane, used was one having the SS1 antibody applied thereonto.

To a 0.75 M tris(hydroxymethyl)aminomethane buffer solution containing 1.0 N sodium hydroxide, added was 1% by weight of polyethylene monooctylphenyl ether (made by Wako Pure Chemical Industries, Ltd.) as a nonionic surfactant, to form a mixture. The mixture was colored blue by further mixing therewith Bromothymol Blue as a pH indicator having a color transition range of pH 5 to 9. This blue colored mixture was designated as a sodium hydroxide-containing aqueous solution containing a pH indicator and a nonionic surfactant (ACD solution). Further, a 0.15 M tris(hydroxymethyl)aminomethane buffer solution containing 1.05 N citric acid was designated as a citric acid-containing tris(hydroxymethyl)aminomethane buffer solution (B solution).

To 100 μL of the saliva, added was 20 μL of the ACD solution. Thereafter, the B solution was added to and mixed with the saliva mixture until it had turned green. The resulting mixture was tested by the immunochromatographic method. In the saliva sample after mixing, clogging of the porous membrane was not observed, and occurrence of the antibody reaction was confirmed.

EXAMPLE 11

Saliva (100 μL) was treated in the following manner, to observe the presence or absence of occurrence of an antibody reaction. In this case, as the saliva, used was one having $2 \times 10^6$ (CFU/mL) of bacteria of *Streptococcus sobrinus*, as measured by a fluorometer, in the saliva. Further, as the porous membrane, used was one having the SS1 antibody applied thereto.

A 1.0 M tris(hydroxymethyl)aminomethane buffer solution containing 1.0 N sodium hydroxide and having 1% by weight of polyethylene glycol monooctylphenyl ether (made by Wako Pure Chemical Industries, Ltd.) as a nonionic surfactant added thereto was designated as a sodium hydroxide-containing aqueous solution containing a nonionic surfactant (AC solution), and a 0.75 M tris (hydroxymethyl) aminomethane buffer solution containing 1.0 N citric acid was designated as a citric acid-containing tris(hydroxymethyl)aminomethane buffer solution (B solution). Further, a pH indicator comprising Methyl Red (D solution) was prepared as a pH indicator having a color transition range of pH 5 to 9.

To 100 μL of the saliva, added was 20 μL of the B solution. Thereafter, the D solution was added dropwise thereto, to color the saliva mixture red, and then, the AC solution was added thereto and mixed therewith until the mixture had turned yellow. The resulting mixture was tested by the immunochromatographic method. In the saliva sample after mixing, clogging of the porous membrane was not observed, and occurrence of the antibody reaction was confirmed.

EXAMPLE 12

Saliva (100 μL) was treated in the following manner, to observe the presence or absence of occurrence of an antibody reaction. In this case, as the saliva, used was one having $2 \times 10^6$ (CFU/mL) of bacteria of *Streptococcus mutans*, as measured by a fluorometer, in the saliva. Further, as the porous membrane, used was one having the SM1 antibody applied thereonto.

A 1.0 M tris(hydroxymethyl)aminomethane buffer solution containing 1.0 N sodium hydroxide was designated as a sodium hydroxide-containing aqueous solution (A solution). Also, to a 1.0 M tris(hydroxymethyl) aminomethane buffer solution containing 1.0 N sodium hydroxide, added was 5% by weight of polyethylene glycol monooctylphenyl ether (made by Wako Pure Chemical Industries, Ltd.) as a nonionic surfactant, to form a mixture. The mixture was colored yellow by further mixing therewith Bromothymol Blue as a pH indicator having a color transition range of pH 5 to 9. This yellow colored mixture was designated as a citric acid-containing tris(hydroxymethyl) aminomethane buffer solution containing a pH indicator and a nonionic surfactant (BCD solution).

To 100 μL of the saliva, added was 25 μL of the BCD solution. Thereafter, the A solution was added to and mixed with the saliva mixture until it had turned green. The resulting mixture was tested by the immunochromatographic method. In the saliva sample after mixing, clogging of the porous membrane was not observed, and occurrence of the antibody reaction was confirmed.

EXAMPLE 13

Saliva (100 μL) was treated in the following manner, to observe the presence or absence of occurrence of an antibody reaction. In this case, as the saliva, used was one having $2 \times 10^6$ (CFU/mL) of bacteria of *Streptococcus mutans*, as measured by a fluorometer, in the saliva. Further, as the porous membrane, used was one having the SM1 antibody applied thereonto.

To a 1.0 M tris(hydroxymethyl)aminomethane buffer solution containing 1.0 N sodium hydroxide, added was 5% by weight of polyethylene glycol monooctylphenyl ether (made by Wako Pure Chemical Industries, Ltd.) as a nonionic surfactant, to form a mixture. The mixture was colored red by further mixing therewith phenolphthalein as a pH indicator having a color transition range of pH 5 to 9. This red colored mixture was designated as a sodium hydroxide-containing aqueous solution containing a pH indicator and a nonionic surfactant (ACD solution). Also, a 1.5 M tris(hydroxymethyl)aminomethane buffer solution containing 1.0 N citric acid and having 5% by weight of polyethylene glycol monooctylphenyl ether (made by Wako Pure Chemical Industries, Ltd.) as a nonionic surfactant added thereto was designated as a citric acid-containing tris-(hydroxymethyl)aminomethane buffer solution containing a nonionic surfactant (BC solution).

To 100 μL of the saliva, added was 20 μL of the ACD solution. Thereafter, the BC solution was added to and mixed with the saliva mixture until it had become colorless. The resulting mixture was tested by the immunochromatographic method. In the saliva sample after mixing, clogging of the porous membrane was not observed, and occurrence of the antibody reaction was confirmed.

EXAMPLE 14

Saliva (100 μL) was treated in the following manner, to observe the presence or absence of occurrence of an antibody reaction. In this case, as the saliva, used was one having $2 \times 10^6$ (CFU/mL) of bacteria of *Streptococcus sobrinus*, as measured by a fluorometer, in the saliva. Further, as the porous membrane, used was one having the SS1 antibody applied thereto.

A 1.0 M tris(hydroxymethyl)aminomethane buffer solution containing 1.0 N sodium hydroxide was designated as a sodium hydroxide-containing aqueous solution (A solution); a 1.0 M tris (hydroxymethyl)aminomethane buffer solution containing 1.05 N citric acid was designated as a citric acid-containing tris (hydroxymethyl)aminomethane buffer solution (B solution); and a sodium phosphate buffer solution containing 10% by weight of 3-[(3-cholamidopropyl)-dimethylammonio]-1-propanesulfonate (made by Sigma Chemical Company) as an amphoteric surfactant was designated as an amphoteric surfactant (C solution), respectively. Further, a pH indicator comprising Phenol Red (D solution) was prepared as a pH indicator having a color transition range of pH 5 to 9.

The B solution (20 μL) was added to 100 μL of the saliva, and the D solution was further added dropwise thereto, to color the mixture yellow. Thereafter, 10 μL of the C solution was added to and mixed with the saliva mixture, and the A solution was further added thereto and mixed therewith until the mixture had turned red. The resulting mixture was tested by the immunochromatographic method. In the saliva sample after mixing, clogging of the porous membrane was not observed, and occurrence of the antibody reaction was confirmed.

COMPARATIVE EXAMPLE 1

Using the saliva sample as used in Example 1, the test was carried out by the immunochromatographic method without using the pre-treatment kit for saliva. As the porous membrane, used was one having the SM1 antibody applied thereonto. In the saliva sample, clogging of the porous membrane occurred, and occurrence of the antibody reaction was not confirmed.

COMPARATIVE EXAMPLE 2

Saliva (100 μL) was treated in the following manner, to observe the presence or absence of occurrence of an antibody reaction. In this case, as the saliva, used was one having $2 \times 10^6$ (CFU/mL) of bacteria of *Streptococcus mutans*, as measured by a fluorometer, in the saliva. Further, as the porous membrane, used was one having the SM1 antibody applied thereto.

A 0.75 M tris(hydroxymethyl)aminomethane buffer solution containing 1.0 N sodium hydroxide and having 0.4% by weight of polyethylene glycol monooctylphenyl ether (made by Wako Pure Chemical Industries, Ltd.) as a nonionic surfactant added thereto was designated as a sodium hydroxide-containing aqueous solution containing a nonionic surfactant (AC solution), and a 1.0 M tris(hydroxymethyl)aminomethane buffer solution containing 1.0 N of any one acid of maleic acid, hydrochloric acid, sulfuric acid, acetic acid, or lactic acid was designated as an acid solution. To 100 μL of the saliva, successively added were 20 μL of the AC solution and 25 μL of the acid solution containing any one of maleic acid, hydrochloric acid, sulfuric acid, acetic acid, or lactic acid, followed by stirring the mixture. The resulting mixtures were each tested by the immunochromatographic method. In the samples, occurrence of the antibody reaction was not confirmed with respect to the treatment with any of the acids.

COMPARATIVE EXAMPLE 3

Saliva (100 μL) was treated in the following manner, to observe the presence or absence of occurrence of an antibody reaction. In this case, as the saliva, used was one having $2 \times 10^6$ (CFU/mL) of bacteria of *Streptococcus mutans*, as measured by a fluorometer, in the saliva. Further, as the porous membrane, used was one having the SM1 antibody applied thereto.

A 1.0 M tris(hydroxymethyl)aminomethane buffer solution containing 1.0 N sodium carbonate and having 1% by weight of polyethylene glycol monooctylphenyl ether (made by Wako Pure Chemical Industries, Ltd.) as a nonionic surfactant added thereto was used (A'C solution), and a 1.0 M tris(hydroxymethyl)aminomethane buffer solution containing 1.0 N citric acid was designated as a citric acid-containing tris (hydroxymethyl) aminomethane buffer solution (B solution).

To 100 μL of the saliva, successively added were 20 μL of the A'C solution and 15 μL of the B solution, to form a mixture. The mixture was tested by the immunochromatographic method. In the sample, occurrence of the antibody reaction was not confirmed.

As it have been described above in detail, it is evident from the Examples and Comparative Examples that the pre-treatment kit for saliva and the pre-treatment method for saliva according to the present invention are a pre-treatment kit and a pre-treatment method for identification and quantitation of mutans streptococci in human saliva by the immunochromatographic method, which can dissolve mucin and glucan present in saliva and act on outer membranes of mutans streptococci, thereby suppressing the chaining and aggregation of mutans streptococci and making proteins present in the mutans streptococci soluble in a simple method, so that the mutans streptococci can pass smoothly through a porous membrane Thus, the present invention is greatly valuable in contributing to the dental field.

While the invention has been described in detail and with reference to specific embodiments thereof, it will be apparent to one skilled in the art that various changes and modifications can be made therein without departing from the spirit and scope thereof.

What is claimed is:

1. A pre-treatment kit for saliva comprising (A) an aqueous solution containing sodium hydroxide; (B) a tris (hydroxymethyl)aminomethane buffer solution containing tartaric acid and/or citric acid; and (C) a nonionic surfactant and/or an amphoteric surfactant, wherein the surfactant (C) is previously mixed with the aqueous solution (A) and/or the buffer solution (B), or is separated from the aqueous solution (A) and the buffer solution (B).

2. The pre-treatment kit for saliva as claimed in claim 1, wherein the nonionic surfactant as the surfactant (C) is one member or a mixture of two or more members selected from the group consisting of polyethylene glycol monooctylphenyl ether, n-octyl-$\beta$-D-glucoside, n-heptyl-$\beta$-D-thioglucoside, n-octyl-$\beta$-D-thioglucoside, nonylphenoxypolyethoxy ethanol, octylphenoxypolyethoxy ethanol, and polyoxyethylene sorbitan monooleate.

3. The pre-treatment kit for saliva as claimed in claim 1 or 2, wherein the amphoteric surfactant as the surfactant (C) is one member or a mixture of two members selected from the group consisting of 3-[(3-cholamidopropyl)-dimethylammonio]-1-propanesulfonate and 3-[(3-cholamidopropyl)-dimethylammonio]-1-hydroxypropanesulfonate.

4. A pre-treatment method for saliva for identification and quantitation of mutans streptococci by the immunochromatographic method, which comprises adding dropwise and mixing (A) an aqueous solution containing sodium hydroxide, (B) a tris(hydroxymethyl)aminomethane buffer solution containing tartaric acid and/or citric acid, and (C) a nonionic surfactant and/or an amphoteric surfactant into and with saliva in an arbitrary order, or adding dropwise and mixing the aqueous solution (A) and the buffer solution (B), with at least one of which the surfactant (C) is mixed, into and with saliva in an arbitrary order, to adjust the pH 5 to 9.

5. The pre-treatment method for saliva as claimed in claim 4, wherein a mixture of the aqueous solution (A) and/or the buffer solution (B) to be added dropwise and mixed, or the aqueous solution (A) and/or the buffer solution (B), with at least one of which the surfactant (C) is previously mixed, and the pH indicator (D) having a color transition range of pH 5 to 9 is used.

6. The pre-treatment method for saliva as claimed in claim 4, wherein during the dropwise addition of the aqueous solution (A) and the buffer solution (B) in dropwise addition and mixing of the aqueous solution (A), the buffer solution (B) and the surfactant (C), or during the dropwise addition of the aqueous solution (A) and the buffer solution (B) in dropwise addition and mixing of the aqueous solution (A) and the buffer solution (B), with at least one of which the surfactant (C) is previously mixed, the pH indicator (D) having a color transition range of pH 5 to 9 is previously added dropwise prior to the dropwise addition of the aqueous solution (A) or the buffer solution (B) to be added dropwise later.

7. A pre-treatment kit for saliva comprising (A) an aqueous solution containing sodium hydroxide; (B) a tris (hydroxymethyl)aminomethane buffer solution containing tartaric acid and/or citric acid; and (C) a nonionic surfactant and/or an amphoteric surfactant, wherein the surfactant (C) is previously mixed with the aqueous solution (A) and/or the buffer solution (B), or is separated from the aqueous solution (A) and the buffer solution (B), wherein (D) a pH indicator having a color transition range of pH 5 to 9 is mixed with the aqueous solution (A) or the aqueous solution (A) having the surfactant (C) previously mixed therewith, and/or buffer solution (B) or the buffer solution (B) having the surfactant (C) previously mixed therewith, or is prepared separately from the aqueous solution (A) or the aqueous solution (A) having the surfactant (C) previously mixed therewith, and the buffer solution (B) or the buffer solution (B) having the surfactant (C) previously mixed therewith.

8. A pre-treatment kit for saliva comprising (A) an aqueous solution containing sodium hydroxide; (B) a tris (hydroxymethyl)aminomethane buffer solution containing tartaric acid and/or citric acid; and (C) a nonionic surfactant and/or an amphoteric surfactant, wherein the surfactant (C) is previously mixed with the aqueous solution (A) and/or the buffer solution (B), or is separated from the aqueous solution (A) and the buffer solution (B), wherein the nonionic surfactant as the surfactant (C) is one member or a mixture of two or more members selected from the group consisting of polyethylene glycol monooctylphenyl ether, n-octyl-$\beta$-D-glucoside, n-heptyl-$\beta$-D-thioglucoside, n-octyl-$\beta$-D-thioglucoside, nonylphenoxypolyethoxy ethanol, octylphenoxypolyethoxy ethanol, and polyoxyethylene sorbitan monooleate, and wherein (D) a pH indicator having a color transition range of pH 5 to 9 is mixed with the aqueous solution (A) or the aqueous solution (A) having the surfactant (C) previously mixed therewith, and/or buffer solution (B) or the buffer solution (B) having the surfactant (C) previously mixed therewith, or is prepared separately from the aqueous solution (A) or the aqueous solution (A) having the surfactant (C) previously mixed therewith, and the buffer solution (B) or the buffer solution (B) having the surfactant (C) previously mixed therewith.

9. The pre-treatment kit for saliva as claimed in claim 8, wherein the pH indicator (D) having a color transition range of pH 5 to 9 is one member selected from the group consisting of Methyl Red, azolitmin, p-nitrophenol, m-nitrophenol, Bromocresol Purple, Bromophenol Red, Chlorophenol Red, Phenol Red, Neutral Red, Bromothymol Blue, phenolphthalein, and Thymolphthalein.

10. A pre-treatment kit for saliva comprising (A) an aqueous solution containing sodium hydroxide; (B) a tris (hydroxymethyl)aminomethane buffer solution containing tartaric acid and/or citric acid; and (C) a nonionic surfactant and/or an amphoteric surfactant, wherein the surfactant (C) is previously mixed with the aqueous solution (A) and/or the buffer solution (B), or is separated from the aqueous solution (A) and the buffer solution (B), wherein the nonionic surfactant as the surfactant (C) is one member or a mixture of two or more members selected from the group consisting of polyethylene glycol monooctylphenyl ether, n-octyl-$\beta$-D-glucoside, n-heptyl-$\beta$-D-thioglucoside, n-octyl-$\beta$-D-thioglucoside, nonylphenoxypolyethoxy ethanol, octylphenoxypolyethoxy ethanol, and polyoxyethylene sorbitan monooleate, wherein the amphoteric surfactant as the surfactant (C) is one member or a mixture of two members selected from the group consisting of 3-[(3-cholamidopropyl)-dimethylammonio]-1-propanesulfonate and 3-[(3-cholamidopropyl)-dimethylammonio]-1-hydroxypropanesulfonate, and wherein (D) a pH indicator having a color transition range of pH 5 to 9 is mixed with the aqueous solution (A) or the aqueous solution (A) having the surfactant (C)

previously mixed therewith, and/or buffer solution (B) or the buffer solution (B) having the surfactant (C) previously mixed therewith, or is prepared separately from the aqueous solution (A) or the aqueous solution (A) having the surfactant (C) previously mixed therewith, and the buffer solution (B) or the buffer solution (B) having the surfactant (C) previously mixed therewith.

11. The pre-treatment kit for saliva as claimed in claim 10, wherein the pH indicator (D) having a color transition range of pH 5 to 9 is one member selected from the group consisting of Methyl Red, azolitmin, p-nitrophenol, m-nitrophenol, Bromocresol Purple, Bromophenol Red, Chlorophenol Red, Phenol Red, Neutral Red, Bromothymol Blue, phenolphthalein, and Thymolphthalein.

12. The pre-treatment kit for saliva as claimed in claim 7, wherein the pH indicator (D) having a color transition range of pH 5 to 9 is one member selected from the group consisting of Methyl Red, azolitmin, p-nitrophenol, m-nitrophenol, Bromocresol Purple, Bromophenol Red, Chlorophenol Red, Phenol Red, Neutral Red, Bromothymol Blue, phenolphthalein, and Thymolphthalein.

* * * * *